US007452390B1

(12) United States Patent
Al-Khalifa et al.

(10) Patent No.: US 7,452,390 B1
(45) Date of Patent: Nov. 18, 2008

(54) CONTROLLED SUPERHEATING OF NATURAL GAS FOR TRANSMISSION

(75) Inventors: Hani Al-Khalifa, Udhailiyah (SA); Donald P. Delevan, Colorado Springs, CO (US); Timothy T. Wilson, George West, TX (US); Abdulrahman Al-Abdullatif, Udhailiyah (SA)

(73) Assignee: Saudi Arabian Oil Company, Dhahran (SA)

( * ) Notice: Subject to any disclaimer, the term of this patent is extended or adjusted under 35 U.S.C. 154(b) by 243 days.

(21) Appl. No.: 10/527,623

(22) PCT Filed: Oct. 23, 2003

(86) PCT No.: PCT/US03/34140

§ 371 (c)(1),
(2), (4) Date: Sep. 22, 2006

(87) PCT Pub. No.: WO2004/038279

PCT Pub. Date: May 6, 2004

(51) Int. Cl.
*C01B 3/32* (2006.01)
*F17D 1/04* (2006.01)
*F17D 1/16* (2006.01)
*F16K 49/00* (2006.01)
*C07C 7/20* (2006.01)
*G05D 23/00* (2006.01)

(52) U.S. Cl. .......................... 48/127.3; 48/190; 48/191; 48/192; 137/13; 137/89; 137/340; 137/599.11; 585/899; 422/105; 422/109

(58) Field of Classification Search ................ 48/127.3, 48/190, 191, 192; 137/13, 89, 340, 599.11; 585/899; 422/105, 109
See application file for complete search history.

(56) References Cited

U.S. PATENT DOCUMENTS 2,873,814 A 2/1959 Maher
(Continued)

*Primary Examiner*—Walter D Griffin
*Assistant Examiner*—Lessanework T Seifu
(74) *Attorney, Agent, or Firm*—Abelman, Frayne & Schwab

(57) ABSTRACT

A method is provided for controlling superheating and temperature of a compressed natural gas stream and the addition of a corrision inhibitor composition for transmission through a pipeline that includes: a. dividing a stream of natural gas discharged from a high pressure gas compressor (106) into a first portion (108) and a second portion (202); b. passing the first portion (108) of the gas from the gas compressor to a heat exchanger (112) to heat the gas to a predetermined temperature; c. passing the first portion of gas (111) exiting the heat exchanger to an aftercooler (114); d. passing the second portion (202) of natural gas discharged from the gas compressor (106) to the aftercooler (114) without passing it through the heat exchanger (112), the second portion of gas and the first portion of gas being mixed at the aftercooler inlet and cooled by the aftercooler and discharged from the aftercooler as a cooled gas stream (116) having a temperature no greater than a first temperature; e. passing the cooled gas stream (116) from the aftercooler to a liquid discharge drum (118) to remove condensate from the cooled gas and discharging from the drum a partially dried gas stream (120) at a second temperature; f. passing the partially dried gas stream (120) from the discharge drum to the heat exchanger (112) in heat exchanging relation with the first portion of gas (108) from the gas compressor, and superheating at least a portion of the gas stream (120) to a third temperature to provide a superheated gas stream (129), the third temperature being controlled by an automated control loop responsive to a differential pressure across the gas compressor (106); and g. passing the superheated gas stream (129) into a transmission tie-line (256) and injecting a predetermined amount of a corrosion inhibitor composition into the tie-line to mix with the superheated gas stream, where the amount of corrosion inhibitor injected is proportioned in response to the third temperature.

16 Claims, 6 Drawing Sheets

U.S. PATENT DOCUMENTS

| | | | |
|---|---|---|---|
| 3,644,107 A | 2/1972 | Clark | |
| 3,765,489 A | 10/1973 | Maly | |
| 3,771,260 A | 11/1973 | Arenson | |
| 4,042,011 A | 8/1977 | Schneider | |
| 4,416,333 A | 11/1983 | Mundhenk et al. | |
| 4,805,674 A | 2/1989 | Knowlton | |
| 4,915,176 A | 4/1990 | Sugier et al. | |
| 5,127,231 A | 7/1992 | Larue et al. | |
| 5,351,756 A | 10/1994 | Minkkinen et al. | |
| 5,816,280 A | 10/1998 | Rojey et al. | |
| 5,983,915 A * | 11/1999 | Rojey et al. | 137/13 |

* cited by examiner

CONTROLLED SUPERHEATING OF NATURAL GAS FOR TRANSMISSION

BACKGROUND OF THE INVENTION

In natural gas transmission operations, wellhead fluids are processed in a gas-oil separation plant (GOSP), to produce dry crude, water, gas and hydrocarbon condensates. The wellhead fluids first enter a high pressure production trap (HPPT) where the gas and some of the water is separated from the crude oil. The remaining oil/water emulsion flows into a low pressure production trap (LPPT) where the oil is flashed at a lower pressure and more gas is separated. The oil/water emulsion is then pumped through a dehydrator and desalter to remove sufficient water and salt to produce product specification crude oil.

The gas from the low pressure production trap is compressed to the pressure of the high pressure production trap and both streams of gas are combined, further compressed and sent to gas plants (GP). In the gas plants, the gas is sweetened to remove sulfur, and sale gas and NGL are produced.

Historically, during the early stages of oil production from a new field in the middle east, only "pilot" GOSPs were required. This is because very little water was produced with the oil and all associated gas was flared. During the late 1970's and early 1980's, the industry decided to develop gas production to generate power for use in petrochemical industries. To that end, GOSPs were upgraded with installation of with a "gas gathering system", the function of which was to efficiently transfer gas from the GOSPs to the gas plants.

In the early designs of the prior art, a typical GOSP had one low pressure ("LP") gas compressor with its auxiliaries and two high pressure ("HP") compressors with one common suction drum. The gas leaving the HP gas compressor entered a shell and tube heat exchanger and then went into a fin-type air cooler having a fan that was designed to decrease the gas temperature to 80° F. in the winter and 133° F. during the summer months. The gas then went into the discharge drum where liquid was dropped. In the final stage, the exit gas entered the cool side of the heat exchanger with a controlled bypass line around it. The GOSP exiting gas temperature was regulated by this control loop. When the GOSP exiting gas temperature dropped below the set point, a valve closed to force more exit gas to flow through the heat exchanger to pick up more heat and raise its temperature. The process was reversed if the temperature exceeded the desired value.

The gas gathering system was originally designed so that the gas leaving each GOSP would remain in the single-phase, dry gas mode until it reached the gas plant. This was accomplished by superheating the gas entering the pipeline network to prevent condensation of any of its components during transport.

The final gas temperature was controlled at 165° F. throughout the year, with 165° F. chosen primarily to assure that the gas mixture would have sufficient superheat to overcome the Joule-Thompson effect that occurred whenever the HP gas compressor recycle valve opened. Since the recycle went directly to the suction side or intake line of the compressor, the recycled gas had to be superheated to prevent any damage to the compressor. A temperature of 165° F. allows about 32° F. for the Joule-Thompson effect to occur before liquid condensate is formed and drawn into the suction side of the gas compressor during the hottest day of the year.

Operations of the system at temperatures above 130° F. proved to degrade the external pipe wrap tape, shortening the life of the tape wrap and necessitating its more frequent repair or replacement.

After this prior art gathering system was operated for many years, it was determined that the fluid steam in the pipeline system could not be maintained in the single-phase dry gas mode 100% of the time. Although originally designed for a single-phase dry gas mode of operation, flow regime, pressure and temperature changes caused a consequent condensation or "liquid drop". The dropped liquid eventually caused corrosion at points in the gas gathering pipeline and repairs were costly.

On the basis of field studies, it was concluded that the gas gathering pipeline network had to operate under various conditions, and 100% single-phase dry gas could not be maintained at all times. The operational mode was changed to two-phase flow from the inlet of the pipeline to the network terminus with addition of a diesel-based corrosion inhibitor in order to protect the pipeline. This was achieved by injecting corrosion inhibitors into the gas streams leaving each GOSP. Diesel oil was injected to saturate the gas stream and change the phase envelope to include the inlet conditions of the stream.

Since the exit gas containing the corrosion inhibitor was in two phases, a film containing corrosion inhibitor formed on the internal pipeline surface. This film acts as a medium for the active ingredients. As a result, the active ingredients travel throughout the system and thereby ensure protection of the pipeline in case condensation forms.

It was also determined that the amount of enhanced corrosion inhibitor required is directly proportional to the temperature of the gas stream. At 165° F. each one million standard cubic feet ("MMSCF") of gas require about one gallon of the diesel-corrosion inhibitor mixture to become saturated and at 130° F. only 0.5 gallon per MMSCF is required for saturation. See FIG. 1. To assure adequate protection, the prior art recommended that the rate of addition should not be lower than 0.5 gallon per MMSCF of gas.

It has been recognized that reducing chemical usage in general can be beneficial to the environment and can also produce substantial cost savings. It is therefore an object of the present invention to provide an improved method of adding corrosion inhibitor compositions that will be more cost effective and reduce chemical usage, and will also be automatated to reduce human error and labor spent on this task.

It is another specific object of this invention to provide an improved process for controlling the temperature and thereby the amount of corrosion inhibitor composition added to a gas stream for transmission from a GOSP.

A further object of the invention is to provide a process and apparatus for reducing the superheated gas temperature to below 165° F., while effectively saturating the gas with less than 1 gallon per MMSCF of corrosion inhibitor.

SUMMARY OF THE INVENTION

The above objects and other advantages are achieved by the method of the invention which includes the steps of carefully controlling the temperature of a gas stream exiting a gas-oil separation plant prior to passing the gas stream into a gas transmission pipeline, measuring the actual temperature of the temperature-controlled gas stream, and adding a predetermined amount of an enhanced corrosion inhibitor composition to the gas stream based on the temperature in order to provide a saturation level of the corrosion inhibitor composition.

In accordance with the present invention, the method is directed to the following features:

1) An automated chemical injection system utilizing an electronic capacity controller (ECC);

2) an automated control loop to regulate the amount of superheat added to the exiting gas, including a modified controller loop of a temperature control valve (TVC) that operates at a remote set point to control the volumetric flow of the gas stream; and 3) means for reducing the outlet temperature in accordance with the remote set point.

As used herein, the term "superheat" means the addition of heat to a gas stream to raise or increase its temperature, and also to the corresponding process step of passing the gas through a heat exchanger for this purpose.

In its broadest scope, the invention contemplates a method of controlling superheating of a compressed natural gas stream for transmission through a pipeline, the method comprising:

a. dividing a stream of natural gas discharged from a high pressure gas compressor into a first portion and a second portion;

b. passing the first portion of the gas from the gas compressor to a heat exchanger to heat the gas to a predetermined temperature;

c. passing the first portion of gas exiting the heat exchanger to an aftercooler;

d. passing the second portion of natural gas discharged from the gas compressor to the aftercooler without passing it through the heat exchanger, the second portion of gas and the first portion of gas being mixed at the aftercooler inlet and cooled by the aftercooler and discharged from the aftercooler as a cooled gas stream having a temperature no greater than a first temperature;

e. passing the cooled gas stream from the aftercooler to a liquid discharge drum to remove condensate from the cooled gas and discharging from the drum a partially dried gas stream at a second temperature;

f. passing the partially dried gas stream from the discharge drum to the heat exchanger in heat exchanging relation with the first portion of gas from the gas compressor, and superheating at least a portion of the gas stream to a third temperature to provide a superheated gas stream, the third temperature being controlled by an automated control loop responsive to a differential pressure across the gas compressor; and g. passing the superheated gas stream into a tie-line and injecting a predetermined amount of an enhanced corrosion inhibitor formulation into the tie-line to mix with the superheated gas stream, where the amount of enhanced corrosion inhibitor injected is proportioned in response to the third temperature.

The process of the present invention is directed to controlling the final temperature of GOSPs gas lines by determining the superheat temperature or heat to be added to the final gas temperature required to prevent or minimize condensate and hydrate formation in the high pressure (HP) compressor recycle and mechanical seal buffer gas lines.

A control loop referred to as XIC receives three signals corresponding to (a) the HP gas compressor suction pressure, (b) the gas compressor discharge pressure and (c) the HP discharge drum temperature. These signals are transmitted to a control circuit, or a controller/processor unit, which can be an appropriately programmed general purpose computer.

The amount of superheat required to maintain the desired condition is directly proportional to the differential pressure across the compressor. The XIC monitors the differential pressure and by means of the TCV adds the required superheat to the HP discharge drum gas stream to increase its temperature. The XIC transmits a remote set point (RSP) signal to the temperature controller. The temperature controller responds according to the set point to close a valve to direct at least a portion of the gas stream to pass through the heat exchanger to pick up heat if the final temperature drops below the desired temperature, and vice versa. A flow meter also transmits a preferably continuous signal to the controller/processor so that the volume of gas to be treated is calculated. A by-pass line is provided at the heat exchanger to deliver any portion of the gas stream that does not pass through the heat exchanger to a gas plant tie-line for dosing with corrosion inhibitor.

Based on the new final temperature, the corrosion inhibitor dosage is adjusted automatically using precision injection pumps equipped with electronic capacity controllers and micro-motion flow meters. Corrosion inhibitor dosage rates are directly proportional to the final gas temperature. As the temperature decreases, the corrosion inhibitor dosage is also decreased.

One preferred enhanced corrosion inhibitor formulation is 2% corrosion inhibitor in 98% diesel oil. In one preferred embodiment of the corrosion inhibitor injection control system of the invention, the mixing of the diesel oil and the corrosion inhibitor occurs at the GOSP using two separate pumps. As a result, one pump is dedicated to injecting diesel oil into the gas tie-line while the second pump injects the corrosion inhibitor. The ECC will automatically adjust the diesel and corrosion inhibitor dosage rates based on signal inputs corresponding to the temperature of the exiting gas and its flow rate.

In addition to assuring that a continuous corrosion inhibiting film is provided along length of the gas lines to thereby minimize corrosion failures, the improved process of the invention has the advantages of reducing the consumption of corrosion inhibitor per volume of gas treated relative to the prior art methods, while ensuring that the required dosage of corrosion inhibitor is injected.

Under the prior art method and apparatus, the dosage was set by the operator. It has been found that the dosage added was actually significantly lower or higher than the prescribed dosage. In accordance with the present invention, the addition is automated and the plant operator is relieved of this task so that his time is optimized.

The method also provides the required superheat to protect the compressor during recycle for surge control and also provides the required superheat to the compressor buffer gas lines or dry seal compressors.

A further benefit of the inventive process is that the life of the external tape wrap coating on gas lines is increased, since its design temperature of 130° F. is not exceeded.

Although the process of the invention is especially suited for use at gas-oil separation plants and other facilities that inject corrosion inhibitor into the gas transmission pipelines, the process can be modified for use in non-GOSP plants.

The process of the invention minimizes the costs associated with corrosion inhibitor chemical dosing by 50% at GOSPs. It improves the reliability and accuracy of the dosage since the system is automated and human error is eliminated. In addition, the process has the additional intangible benefit of permitting the operator to attend to other duties in lieu of continuously monitoring and manually adjusting the dosage. Equally importantly, the process of the invention provides gas line protection for a longer period of time.

BRIEF DESCRIPTION OF THE DRAWINGS

The invention will be further described below in conjunction with the attached drawings, where.

DETAILED DESCRIPTION OF THE PREFERRED EMBODIMENTS

Figure 1:
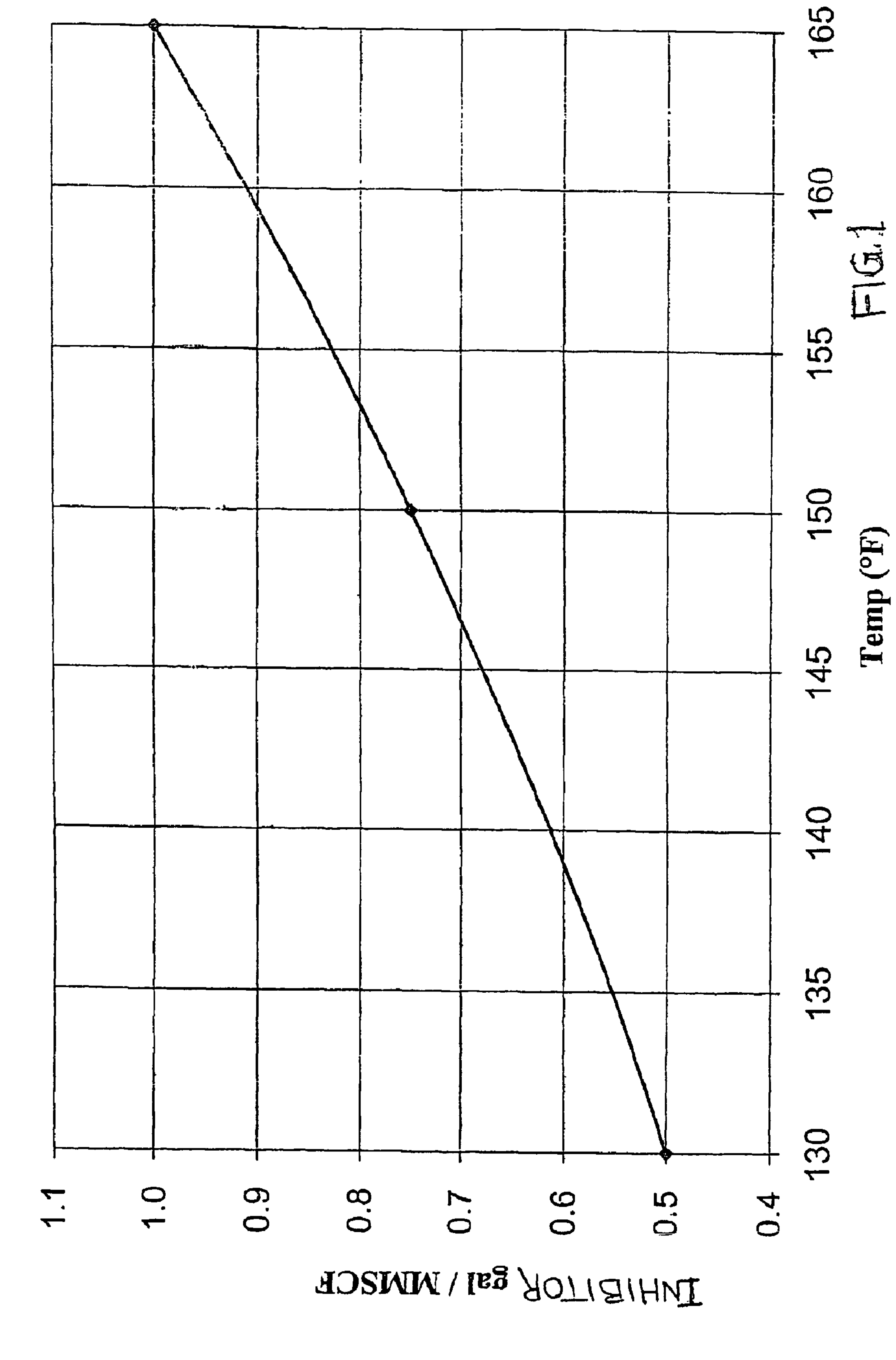
FIG. 1 is a graph of corrosion inhibitor requirements vs. temperature.
Figure 2:
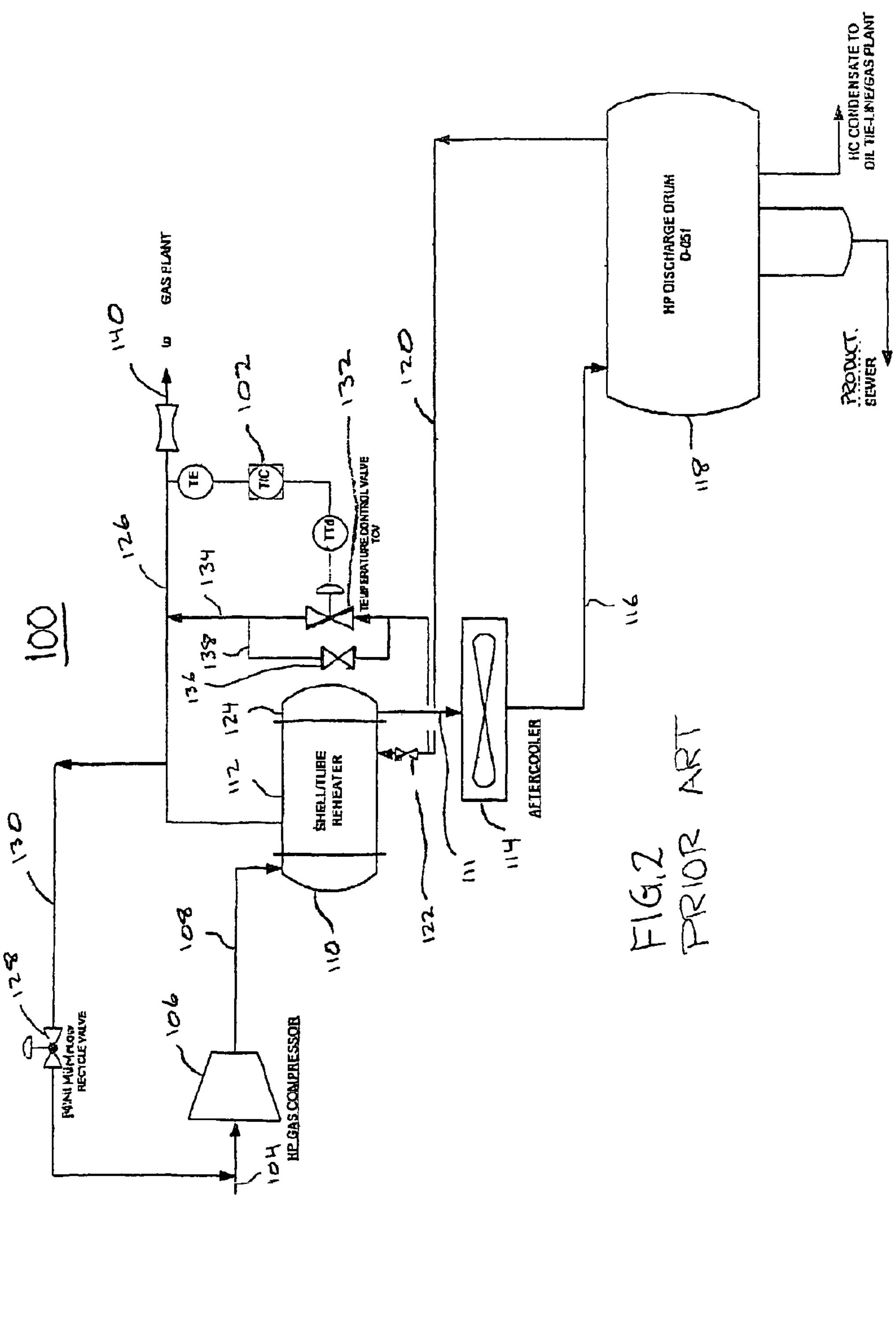
FIG. 2 PRIOR ART
FIG. 2 is a schematic illustration of a conventional GOSP of the prior art.

As noted above in the discussion of the prior art, FIG. 1 reveals the differences between design and actual operational conditions and FIG. 2 shows the clear relationship between temperature and corrosion inhibitor requirements.

Figure 3:
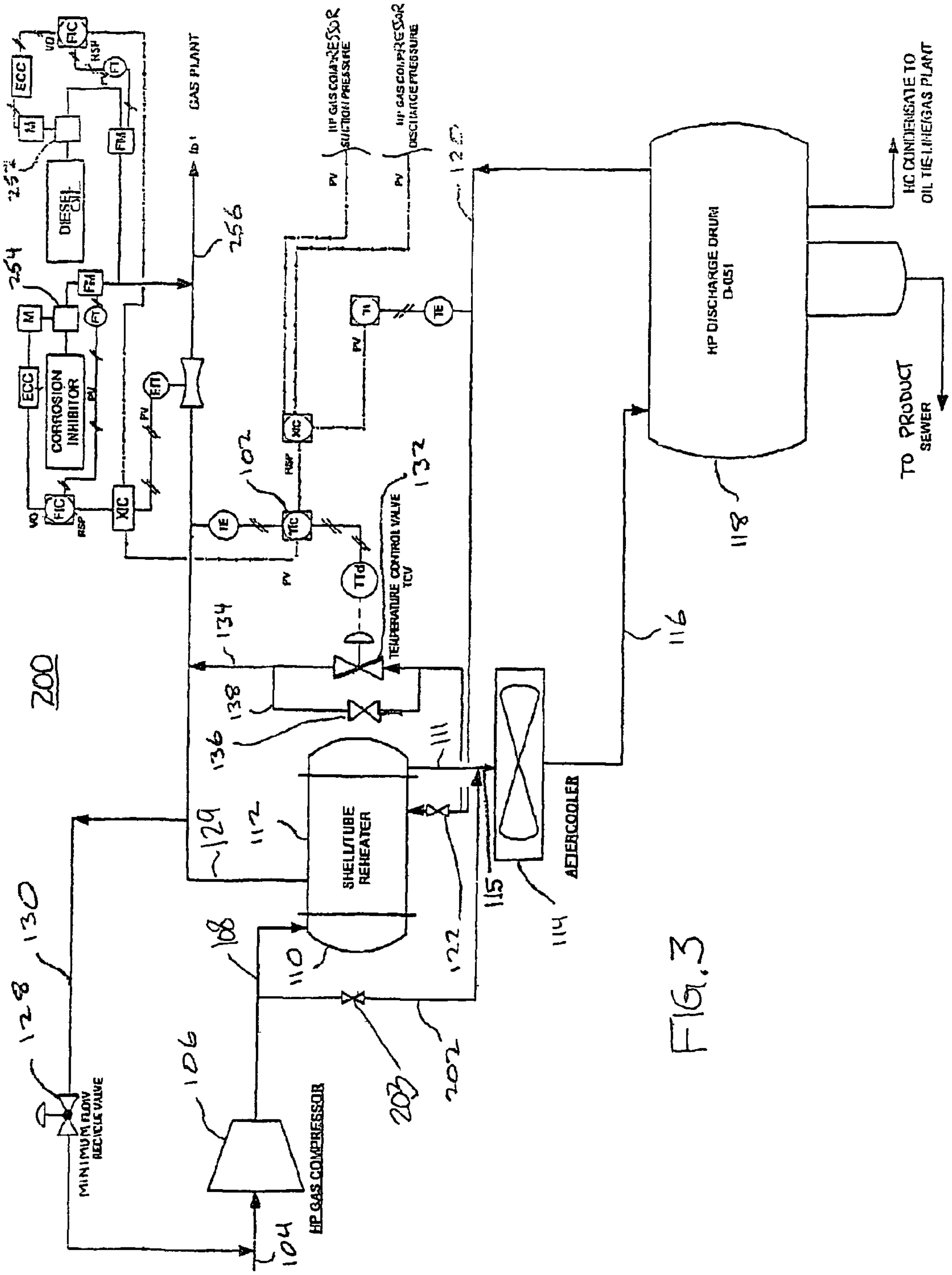
FIG. 3 is a schematic illustration of a GOSP employing an embodiment of the superheating of natural gas for transmission in accordance with the present invention.

FIG. 3 illustrates the operation of a conventional GOSP 100, operating with a temperature control valve (TIC-0241074) 102 set at 165° F. and with 1 gal/MMSCF of enhanced Corrosion inhibitor. The gas in line 104 flows through the HP gas compressor 106 and thence through line 108 to the tube side 110 of a shell and tube heat exchanger, or reheater, 112. From the tube side 110, the gas flows through line 111 to an aftercooler 114 including two two-fan bay induced draft aftercoolers. The aftercooler 114 cools the gas a temperature in the range of 110-133° F. in the summertime and down to 80° F. in the wintertime.

The gas then flows through line 116 to the HP discharge drum 118 where the generated condensate is knocked out. The purified gas flows from the top of the drum 118 through line 120 and passes through 100% open butterfly valve 122 to the shell side 124 of the reheater 110 where it is superheated to about 165° F. The superheated gas output from the shell side 124 flows through line 126 to the gas plant, the gas stream being under the control of a recycle valve 128 on recycle line 130. If the gas temperature downstream of the reheater 110 in the line 126 increases above 165° F., a control valve (TCV-024/074) 132 opens, allowing some of the gas to flow through line 134 to line 126 to bypass the shell side 124, thereby controlling the superheat and reducing the temperature. The purpose of reheating the gas to 165° F. is to raise it further from its dewpoint, especially during summer months, where the gas dew point is 110-130°.

For purposes of comparison with the present invention, a bypass valve 136 is shown in parallel with the TCV 132 on line 138, but valve 136 is closed in this system.

To prevent internal corrosion in the gas pipeline from the GOSP to the gas plant, an enhanced corrosion inhibitor is injected downstream of the reheater 110 into tie-line 140. The preferred enhanced corrosion inhibitor composition is 98% diesel with 2% active ingredient. The current dosage is 1 gallon/MMSCFD at 165° F. final temperature control. The enhanced corrosion inhibitor is injected to saturate the gas stream going to the gas plant. If the gas leaving the GOSP is superheated (i.e., undersaturated), some of diesel in the enhanced corrosion inhibitor will flash into the vapor phase, thereby saturating the gas. Having the gas saturated assures that hydrocarbons will always be present to wet the internal pipe surface and thereby provide an inhibited hydrocarbon film along the pipe.

Figure 4:
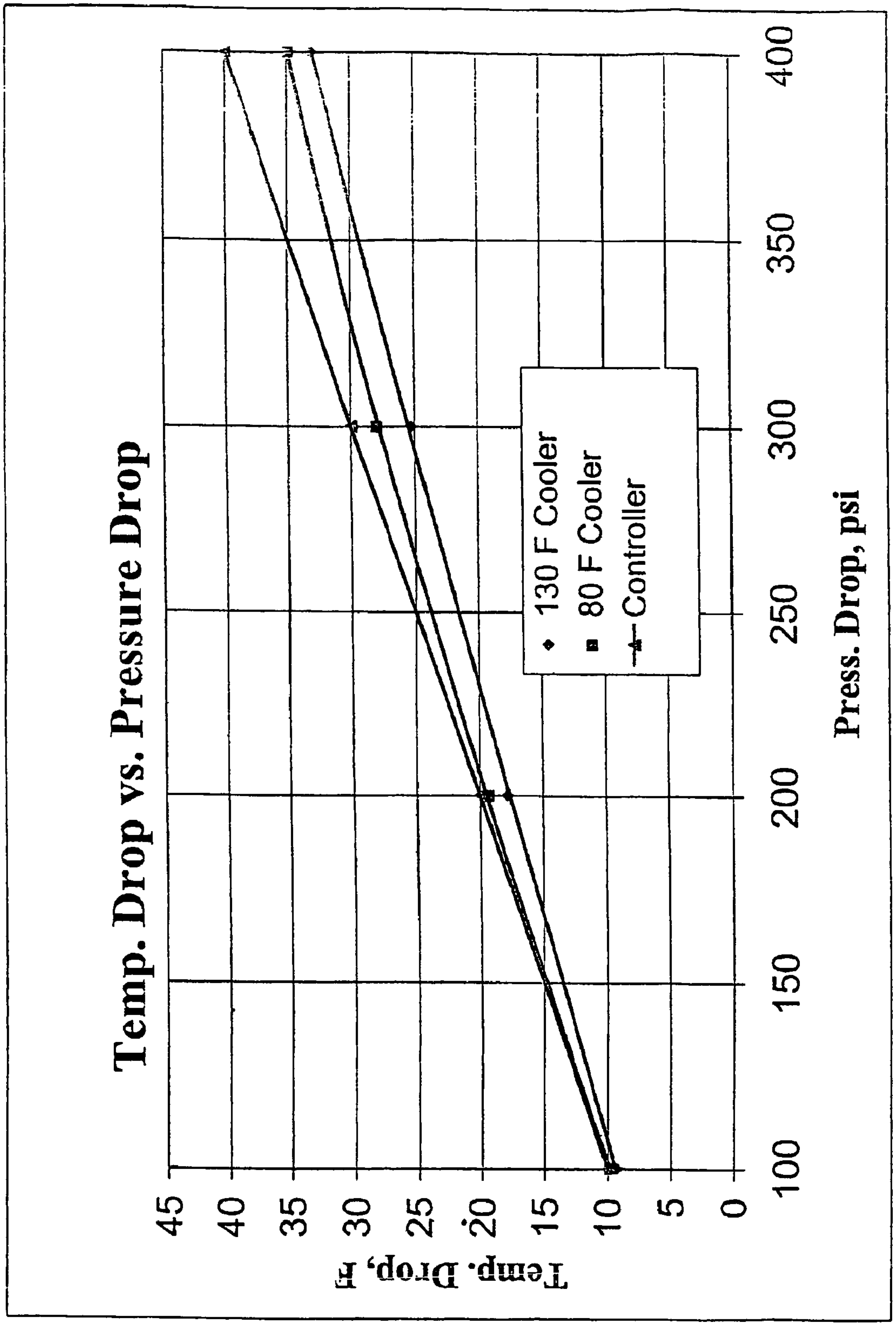
FIG. 4 is a plot of temperature drop vs pressure drop for the discharge drum.

FIG. 4 illustrates a preferred embodiment of a GOSP 200 implementing the process in accordance with the present invention. In contrast with the conventional system 100 described above, this embodiment of the present invention sets the temperature control valve 102 at 130° F. with bypass valves open, and a new enhanced corrosion inhibitor control system 250 is installed. The temperature control valve 102 is configured to operate in a remote set point (RSP) mode, with the bypass valve 132 100% open. In addition, a new bypass 202, preferably a 12" bypass, is provided for the reheater tube side 110.

As mentioned earlier, the current enhanced corrosion inhibitor is composed of a solution of 98% diesel and 2% corrosion inhibitor. In the new corrosion inhibitor system 250, the mixing of the diesel and the corrosion inhibitor is done at the control system 250 using two separate pumps 252, 254. The first pump 252 is dedicated to adding diesel to the gas tie-line 256, while the second pump 254 will pump in normal corrosion inhibitor.

The temperature control valve 102 is set at 130° F. at all times. However, in the system of this embodiment, some superheat is added to raise the final temperature. The purpose is to prevent condensate and hydrate formation in the HP compressor recycle and the buffer gas lines 130, 202. The processor/controller 210 receives three signals: the HP gas compressor suction pressure, the discharge pressure, and the HP discharge drum temperature. As discussed above, the amount of superheat required is directly proportional to the differential pressure across the HP compressor 106. See FIG. 1. The processor/controller 210 determines the differential pressure and adds the required superheat to the HP discharge drum temperature. Then, the processor/controller 210 sends the remote set point (RSP) to the temperature control valve 102. The processor/controller 210 also automatically signals for the adjustment of the diesel and corrosion inhibitor dosage rates based on the signal inputs from the temperature control valve 102 and the measured gas flowrates.

A twelve inch bypass line 202 is installed around the reheater tube side 110. This divides the gas on line 108 from the HP gas compressor 106 so that some or most of the gas bypasses the reheater tube side 110 and flows directly to the aftercooler 114. In this system, the aftercooler 114 provides most of the cooling, and as a result the outlet temperature of the aftercooler 114 will not increase significantly, and will not be higher than 133° F. The aftercooler 114 is designed to achieve a 133° F. outlet temperature at full load.

Butterfly valve 202 on the reheater shell side 110 is kept fully open. A portion of the gas flows through the shell side 110 and the remaining gas flows through the temperature control valve 132. As a result, about 75% of the pressure drop normally lost through the reheater 112, is recovered for compressor power savings.

The system in accordance with the present invention has many advantages. First, it reduces enhanced corrosion inhibitor consumption, thereby effecting a substantial and significant cost savings. It also ensures that the prescribed amount of enhanced corrosion inhibitor composition is injected.

The system in accordance with the present invention reduces the HP gas compressor power consumption by eliminating most of the pressure drop across the reheater. The lower temperature maintains the gas pipeline external tape wrap in good condition. The lower superheat temperature e.g., 130° F., or less than 130° F., will also aid in preserving the pipe line from external corrosion if it is not already damaged.

Furthermore, the system and method of operation of the invention provides the required superheat to protect the compressor during recycle for surge control. Also, it provides the required superheat to dry seal compressor buffer gas lines. Installation of a system at the GP to inject the accumulated liquid results in no liquid being flared. Although somewhat more liquid may collect in the GP slug catchers, this material can be easily processed and this increase in liquid collections for disposal is far outweighed by the advantages of the process.

The results of the following example further demonstrate the advantages of the present invention. The evaluation was conducted in facilities located in a desert climate having large temperature changes between the summer and winter seasons and extremely high daytime temperatures, especially during the summer.

Example

One week prior to the evaluation of the process of the invention, data collection was initiated at the six GOSPs and the GP test facilities for the purpose of comparing the conditions at the existing final gas temperature of 165° F. with the conditions of the superheat reduction process in accordance with the invention. The superheat reduction was started by reducing the exiting gas temperature setting from 165° F. to 130° F. at the six GOSPs feeding one separate pipeline network. This pipeline network terminated at a designated slug catcher drum at the gas plant. The object of the test was to quantify the amount of liquid removed from the pipeline at the gas plant. The protocol was conducted twice: first under desert summer conditions and then under desert winter conditions.

Four types of process data were gathered:

1. The amount of liquid collected at the GP slug catchers and its effect on GP operations.

2. The minimum superheat that GOSPs' operation must maintain.

3. Identification of any process change causing significant liquid hold-up in the line.

4. A determination of whether the reduction in the enhanced corrosion inhibitor provide the required protection along the entire pipeline.

Specific superheat reduction process advantages to be verified were as follows:

1. To minimize the GOSP operating cost in terms of electrical power and enhanced corrosion inhibitor addition by reducing the pressure drop across the reheater and optimizing the GOSPs exit gas temperature.

2. To confirm the effect of lowering the temperature setting of the temperature control valve on the gas pipeline operation.

Each of the seasonal tests was conducted in three phases. During Phase I, the final gas temperature leaving the GOSP was reduced from 165° F. to 130° F. and the enhanced corrosion inhibitor dosage was reduced by 50%. The amount of liquid collected at GP slug catchers during this phase varied from zero BPD to 102 BPD. The average liquid rate at 165° F. was about 10 BPD; the average liquid rate at 130° F. was about 20 BPD.

During Phase II, the final gas temperature varied based on the HP discharge drum temperature. The enhanced corrosion inhibitor dosage in this phase varied from 10 BPD to 158 BPD. The average liquid collected during this phase was about 92 BPD.

During Phase III, the effect of adding 20-30° F. of superheat was tested. The average amount of liquid collected during this phase was about 28 BPD.

A detailed description of the procedures and results of each of the three phases follows.

Phase I

As an initial procedure, the lines were scraped to ensure that there was no liquid hold-up or sludge accumulation in the lines prior to collecting the data. The scraping showed that there was neither sludge nor liquid holdup in either pipeline.

Next, the final gas temperature was lowered to 130° F. at HD-1 and HW-4 by changing the setting on the final gas temperature controllers from 165° F. to 130° F. and fully opening the bypass valves of the temperature control valves. If the final temperature did not decrease to 130° F., the shell side of the reheater was partially bypassed by closing the butterfly valve on the shell inlet. The addition rate of the enhanced corrosion inhibitor was reduced from 1.0 gal/MMSCF to 0.5 gal/MMSCF.

The lines were again scraped to determined whether the superheat reduction at HD-1 and HW-4 resulted in any liquid hold-up or sludge accumulation. The scraping showed that there was neither sludge nor liquid hold-up in the lines.

Thereafter, HW-2 and HW-3 were included, and the GOSP final gas temperature was lowered to 130° F. The enhanced corrosion inhibitor addition rate to those streams was also lowered from 1.0 gal/MMSCF to 0.5 gal/MMSCF. The lines were again scraped to determine whether the superheat reduction at four GOSPs caused any sludge or liquid hold-up. The scraping showed that there was neither sludge nor liquid hold-up in the lines.

Thereafter, U-14 and U-13 were included and the GOSP final gas temperature was lowered to 130° F. The enhanced corrosion inhibitor addition rate to those streams was also lowered from 1.0 gal/MMSCF to 0.5 gal/MMSCF. The lines were scraped again to see if the superheat reduction at all six GOSPs resulted in any sludge or liquid hold-up. The scraping showed that there was neither sludge nor liquid hold-up in the lines.

Phase II

The purpose of this phase was to allow variations based on HP discharge drum temperature. In order to avoid upsets at the GP due to high liquid accumulations in slug catchers D-051 and D-054, the test was conducted in two steps:

Step 1:

The set point of the temperature controllers [TIC-024/074] was lowered to 115° F. and the bypasses of the temperature control valves [TCVs-024/074] were fully opened. Where the final temperature could not be decreased to 115° F., the butterfly valve on the reheater shell side was fully closed. The butterfly valve was slightly opened when the temperatures decreased to below 115° F. The enhanced chemical injection was maintained at 0.5 gal/MMSCF.

Step 2:

Step 1 showed that operating at temperatures near or at the gas dewpoint was safe and would not generate unmanageable amounts of liquid at the GP slug catchers, [D-051 and D-054]. Consequently, the evaluation proceeded to the next step of varying HP discharge drum temperature at all six GOSPs as follows:

(a) the temperature control valves [TCVs-024/074] were put on manual mode and fully opened;

(b) the bypasses of these valves [TCV-024/074] were kept open all the time; and (c) the butterfly valve on the shell side inlet was fully closed.

Phase III

The effect of adding 20° to 30° F. of superheat was determined as follows:

1. The set point of the temperature controllers [TIC-024/074] was raised to 130° F.

2. The butterfly valve on the reheater shell side inlet was fully opened, and the bypass valves for the temperature control valves [TCV-024/074] were fully opened.

3. The addition rate of enhanced corrosion inhibitor dosage was raised to 0.8 gal/MMSCF.

The lines were scraped. The scraping revealed that there was neither sludge nor liquid hold-up in the lines.

During Phase I (controlling at 130° F.), the maximum liquid that arrived at slug catchers D-051 and D-054 was about 102 BPD for both slug catchers. The average was about 20 BPD. The liquids arrived as a mist. It would take about 15 minutes to accumulate about 10 BBL of liquid in the slug catcher. No slug flow into the slug catchers was observed.

During Phase II (floating on HP discharge drum temperature), the maximum liquid arriving at the GP slug catchers was about 158 BPD. The average was about 92 BPD. The maximum liquid collected at the slug catchers during a run was about 260 B/12 hours. On that day, liquid was received during a 12-hour period. Liquid was not observed during the other 12-hour period. Consequently, the total liquid received at the slug catchers on that occasion was 260 BPD. As with Phase I, no slug flow into the slug catchers was observed.

During Phase III (20-30° F. of superheat), the maximum liquid arriving at GP slug catchers was about 66 BPD. The average was about 28 BPD. In this mode of operation the liquid collected in only one slug catcher [D-054].

Due to a swing in the discharge drum temperature at the GOSP, liquid arrival at GP slug catchers occurred principally between noon and midnight. As the discharge drum temperature increased during the day, richer gas was sent to the GP and, as a result, more condensation occurred in the gas pipeline.

Liquid collected at GP slug catchers during Phase II was well below the established limit of 400 BPD for both slug catchers.

Samples of the gas leaving the slug catchers were taken before and during the runs and no significant changes in the composition of the sour gas exiting the slug catchers were observed.

Samples taken from the liquid collected at the GP slug catchers before and during the runs showed corrosion inhibitor presence. The concentration of the enhanced corrosion inhibitor varied from 40 to 1700 ppm.

Figure 5:
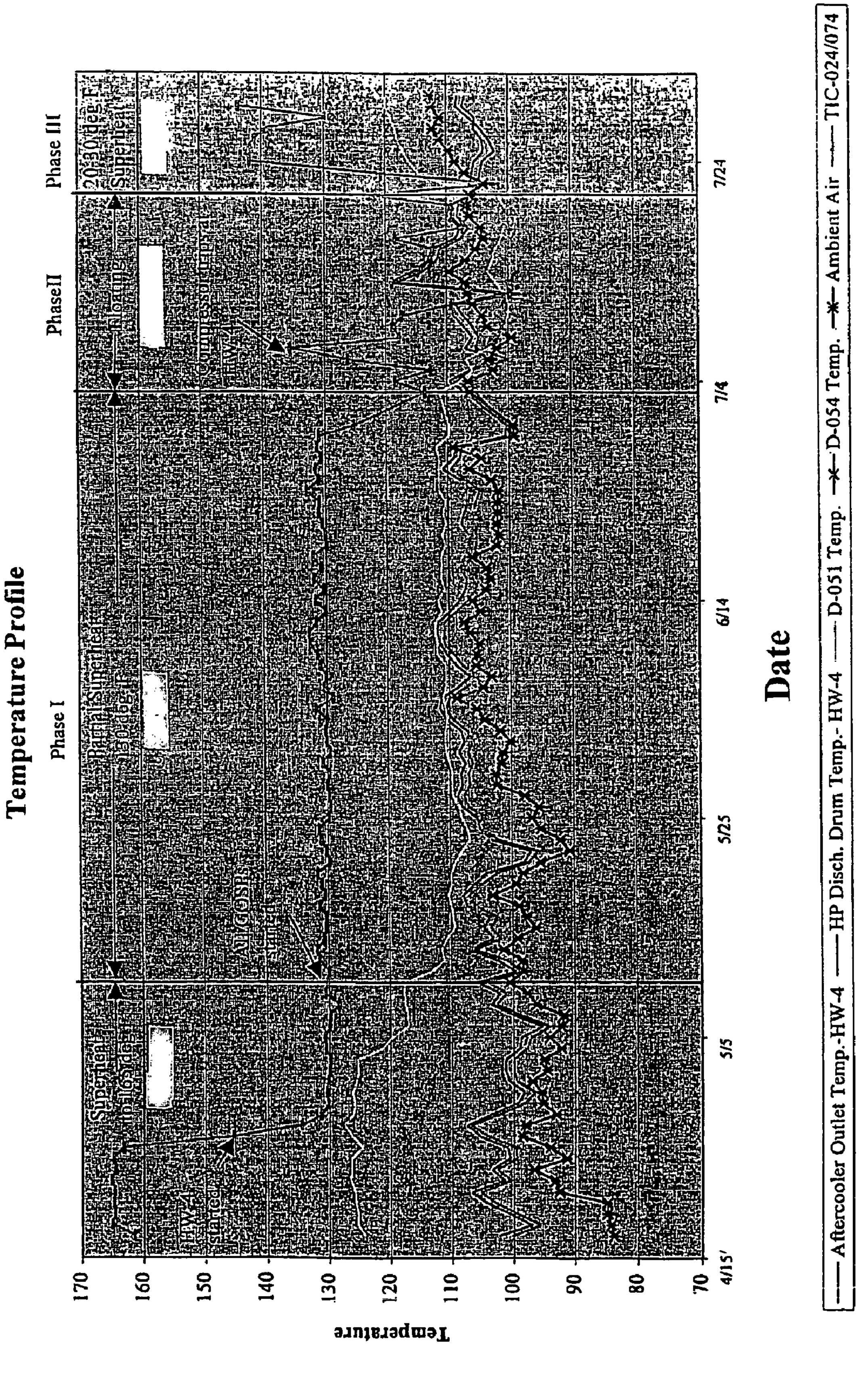
FIG. 5 is a temperature profile for different phases of the test.
Figure 6:
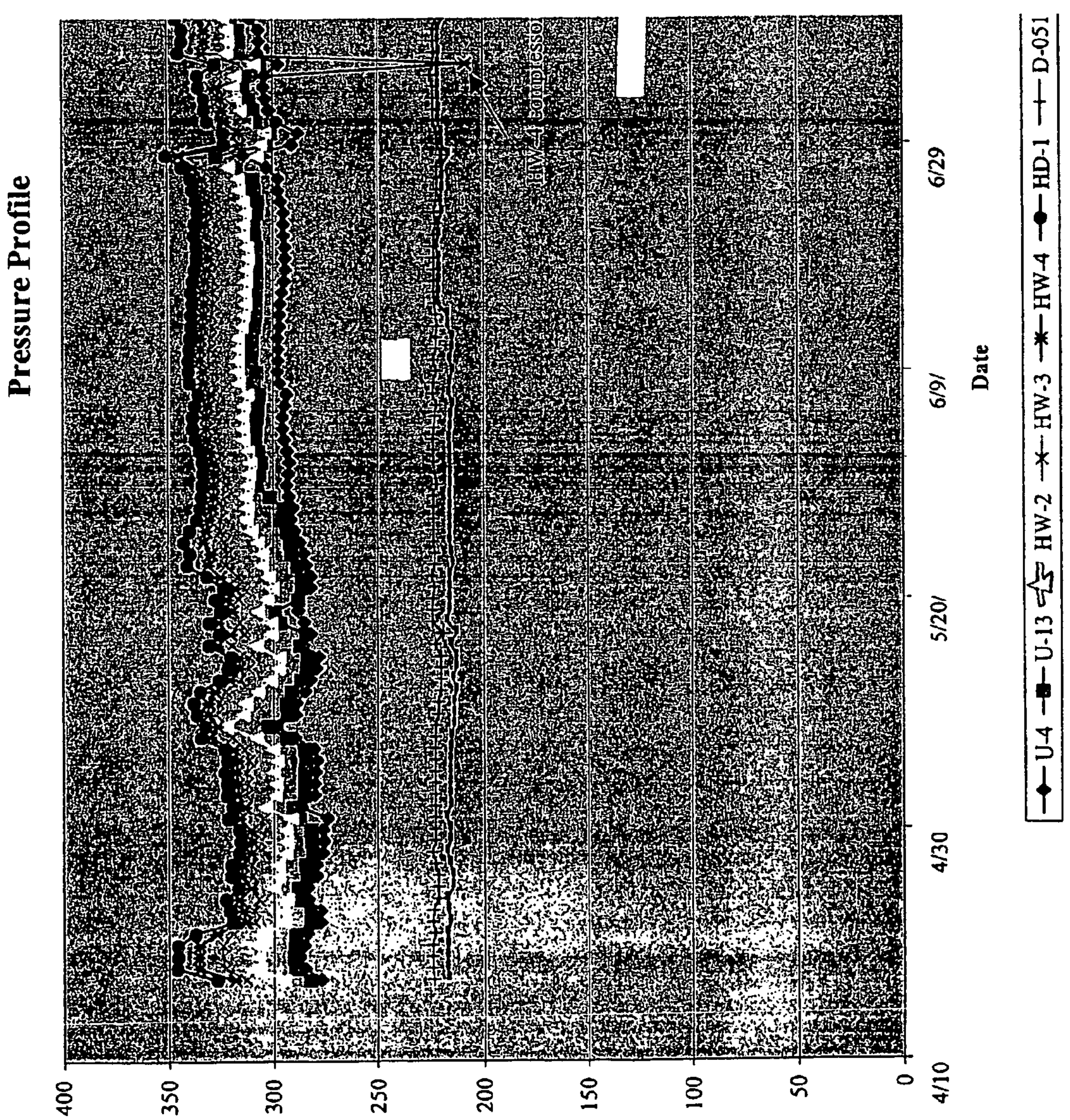
FIG. 6 is a pressure profile for different phases of the test.

FIGS. 5 and 6 show the test temperature and pressure profiles, respectively. The GOSP operation was not adversely affected by the superheat reduction. The pressure profile was to be relatively constant throughout the run. The temperature profile shows that the slug catcher temperatures were above the ambient temperature prior to reducing the superheat temperature. The slug catcher temperatures decreased gradually as the GOSPs reduced the superheat temperature.

Prior to Phase I, the slug catcher temperature varied from 115°-125° F. The temperature started to decrease as more GOSPs were added. During Phase I, the slug catcher temperature was at 105°-110° F., slightly higher than the ambient air temperature. During Phase II, the slug catcher temperature stayed at 100°-103° F., which is below the ambient air temperature. During Phase III, the slug catcher temperature climbed to 110°-120° F. as the GOSPs added 20°-30° F. of superheat to the gas. This data shown is representative of all tested GOSPs and was taken from a GOSP that runs at maximum design capacity most of the time.

During Phase II of the test, the cooling load was fully achieved by the aftercoolers. The increase in the GOSP aftercooler outlet temperature was insignificant. See FIG. 4.

The maximum liquid that arrived at GP slug catchers was about 66 BPD. The average was about 28 BPD.

Due to a swing in discharge drum temperature at the GOSP, more liquid arrived at the GP slug catchers between noon and midnight. As the discharge drum temperature rose during the daytime, richer gas was sent to the GP, and as a result more condensation occurred in the gas pipeline.

It was noted that the exiting gas temperature could not be maintained at 130° F. during very hot days in the desert climate where the work was conducted even though the TCV was fully open and its bypass was fully open. This is because the temperature at the discharge drum is initially very high and the amount of the exiting gas that passes through the heat exchanger is enough to raise the outlet temperature above 130° F.

Samples of gas leaving the slug catchers were taken before and during the test and no significant change in the composition of the sour gas exiting the slug catchers was observed.

Samples taken from the liquid collected at the GP slug catchers before and during the run showed the presence of corrosion inhibitor. This confirmed that the corrosion inhibitor was carried by a film of liquid on the pipeline internal surface throughout the pipeline network to the gas plant and that the pipeline was well protected.

Theoretically, maximum electrical power cost reduction could be obtained by totally removing the reheater. The average compressor horsepower readings dropped by 100 hp per compressor when the pressure drop across the reheater was reduced by fully opening the TCV and its bypass, for a total of 500 HP for the three GOSPs. More power can be saved by fully bypassing the reheater, specifically, the tube side.

As noted above, the final gas temperature could not be maintained at 130° F. during the peak daytime temperature period while simultaneously maintaining a minimum pressure drop across the reheater. The temperature rose to approximately 150° F. for 2 to 4 hours during the afternoon and the enhanced corrosion inhibitor rate was raised to 0.8 gal/MMSCF from 0.5 gal/MMSCF. This represents a 20% chemical saving; up to 50% saving can be achieved utilizing an automated corrosion inhibitor system.

The results of the improved process demonstrated the technical and economic feasibility of reducing the superheat temperature at the GOSP to saturated conditions. As depicted in FIG. 4, the gas in the discharge drum is in equilibrium with the liquid phase. That is, at discharge drum conditions, the gas is at its dewpoint and the liquid is at its bubble point. Since the enhanced corrosion inhibitor is injected downstream of the reheaters and as a result saturates the gas, the gas can be sent saturated as is from the HP discharge drum and partially or fully bypass the reheater shell side. Under these operating conditions, the enhanced corrosion inhibitor dosage can be decreased, since it is directly proportional to the final gas temperature. Also, if the reheater can be eliminated or at least if the pressure drop across it is minimized, then the HP gas compressor power consumption will be decreased as well.

An automated enhanced corrosion inhibitor and superheat control system with installation of a 12" bypass on the reheater tube side results in the recovery of 75% of the pressure drop across the reheater and reduces the enhanced corrosion inhibitor costs by 72%.

It was also found that the superheat reduction did not result in loss of incremental value of NGL. The total maximum condensate generated from all of the GOSP-associated gas and Khuff gas wells that are connected to GOSPs is about 2200 BPD of which 90% or more is Khuff condensate and the remainder is GOSP-associated gas condensate.

The data revealed that the temperature increase at the aftercooler outlet was not significant, being only 3° to 6° F. Furthermore, the aftercooler outlet temperatures did not exceed the aftercooler design outlet temperature of 133° F. In fact, the data established that the aftercoolers were able to achieve lower than design outlet temperature most of the time.

Pipeline pressure was also found to be relatively constant throughout the operation of the process of the invention and no slug flow in the GP slug catchers was observed. The extremes in operating conditions associated with the seasonal desert temperatures did not adversely effect the results.

The above example and data establish the advantages of the process of the invention. Various modifications to specific equipment installations and operating conditions will be apparent to those of ordinary skill in the art and the invention is to be limited only by the scope of the claims that follow.

We claim:

1. A method of controlling superheating of a compressed natural gas stream for transmission through a pipeline, the method comprising:

a. dividing a stream of natural gas discharged from a high pressure gas compressor (106) into a first portion (108) and a second portion (202);

b. passing the first portion (108) of the gas from the gas compressor to a heat exchanger (112) to heat the gas to a predetermined temperature;

c. passing the first portion of gas (111) exiting the heat exchanger to an aftercooler (114);

d. passing the second portion (202) of natural gas discharged from the gas compressor (106) to the aftercooler (114) without passing it through the heat exchanger (112), the second portion of gas and the first portion of gas being mixed at the aftercooler inlet and cooled by the aftercooler and discharged from the aftercooler as a cooled gas stream (116) having a temperature no greater than a first temperature;

e. passing the cooled gas stream (116) from the aftercooler to a liquid discharge drum (118) to remove condensate from the cooled gas and discharging from the drum a partially dried gas stream (120) at a second temperature;

f. passing the partially dried gas stream (120) from the discharge drum to the heat exchanger (112) in heat exchanging relation with the first portion of gas (108) from the gas compressor, and superheating at least a portion of the gas stream (120) to a third temperature to provide a superheated gas stream (129), the third temperature being controlled by an automated control loop responsive to a differential pressure across the gas compressor (106); and g. passing the superheated gas stream (129) into a tie-line (256) and injecting a predetermined amount of an enhanced corrosion inhibitor formulation into the tie-line to mix with the superheated gas stream, where the amount of enhanced corrosion inhibitor injected is proportioned in response to the third temperature.

2. The method of claim 1, wherein the enhanced corrosion inhibitor formulation is a mixture of diesel oil and a conventional corrosion inhibitor, and wherein in step (g), the diesel oil is injected into the tie-line using a first pump and the corrosion inhibitor is injected into the tie-line using a second pump.

3. The method of claim 1, wherein in step (f), the automated control loop receives first and second input signals corresponding to the suction pressure of the gas compressor and the discharge pressure of the gas compressor, respectively, the control loop calculating the differential pressure in response to the first and second input signals.

4. The method of claim 3, wherein in step (f), the control loop receives a third input signal corresponding to the second temperature of the partially dried gas output from the discharge drum, the control loop controlling the third temperature in response to the second temperature and the value of the differential pressure across the gas compressor.

5. The method of claim 4, wherein in step (f), the control loop controls the third temperature by determining an amount of superheat to be added to the partially dried gas in the heat exchanger in order to raise the temperature of the gas from the second temperature to the third temperature.

6. The method of claim 5, wherein in step (f), after the control loop determines the amount of superheat, the control loop transmits a remote set point to a temperature controller of the heat exchanger.

7. The method of claim 1, wherein in step (f), the control loop transmits a remote set point to a temperature controller of the heat exchanger to control the third temperature.

8. The method of claim 1, wherein the heat exchanger is a shell and tube heat exchanger and the first portion of pressurized gas passes through the tubes of the heat exchanger.

9. The method of claim 1, wherein the third temperature is about 130° F.

10. The method of claim 1, wherein the amount of enhanced corrosion inhibitor added is sufficient to saturate the gas stream entering the pipeline at the third temperature.

11. A system for the controlled superheating of compressed natural gas for transmission through a pipeline, comprising:

a gas compressor for raising the pressure of the natural gas for transmission through the pipeline;

a heat exchanger;

a first path connecting said gas compressor to said heat exchanger, a first portion of pressurized gas flowing from said gas compressor to said heat exchanger through said first path;

an aftercooler;

a second path connecting said heat exchanger to said aftercooler, the first portion of heated gas flowing from said heat exchanger to said aftercooler through said second path;

a bypass connecting said gas compressor to said aftercooler, a second portion of the natural gas flowing from said gas compressor to said aftercooler through said bypass without passing through said heat exchanger, the second portion of gas and the first portion being mixed at said aftercooler and cooled by said aftercooler to be output from the aftercooler as cooled gas having an output temperature no greater than a first temperature;

a discharge drum;

a third path connecting said aftercooler to said discharge drum, the cooled gas flowing from said aftercooler to said discharge drum through said third path, the cooled gas in said discharge drum having generated condensate removed therefrom to become partially dried gas at a second temperature;

a fourth path connecting said discharge drum to said heat exchanger, the partially dried gas flowing from said discharge drum to said heat exchanger through said fourth path, the partially dried gas being superheated to a third temperature in said heat exchanger to become superheated gas;

a control loop for controlling the third temperature in response to the differential pressure across said gas compressor;

a tie-line extending from said heat exchanger, the superheated gas flowing from said heat exchanger into said tie-line; and pumping means for injecting a controlled amount of an enhanced corrosion inhibitor formulation into said tie-line for mixing with the superheated gas, where the amount of enhanced corrosion inhibitor formulation is controlled automatically in response to the third temperature.

12. The system of claim 11, wherein said control loop transmits a remote set point to a temperature controller associated with said heat exchanger to control the third temperature.

13. The system of claim 11, wherein the heat exchanger is a shell and tube heat exchanger.

14. The system of claim 11 which further comprises a fifth path connecting said discharge drum to the tie line, whereby a controlled portion of the partially dried gas bypasses the heat exchanger.

15. The system of claim 14, wherein the amount of any partially dried gas passing through the fifth path is controlled by the control loop in response to the second temperature.

16. The system of claim 15 which further comprises a temperature control valve for admitting partially dried gas to pass through said fifth path.

* * * * *